United States Patent
Wakai

(10) Patent No.: US 10,451,699 B2
(45) Date of Patent: Oct. 22, 2019

(54) IMAGE PROCESSING DEVICE AND MRI APPARATUS

(71) Applicant: TOSHIBA MEDICAL SYSTEMS CORPORATION, Otawara-Shi (JP)

(72) Inventor: Satoshi Wakai, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 60 days.

(21) Appl. No.: 15/295,380

(22) Filed: Oct. 17, 2016

(65) Prior Publication Data
US 2017/0227620 A1  Aug. 10, 2017

(30) Foreign Application Priority Data

Feb. 9, 2016  (JP) ................ 2016-022378

(51) Int. Cl.
G01V 3/00 (2006.01)
G01R 33/563 (2006.01)
G01R 33/48 (2006.01)
A61B 5/00 (2006.01)
A61B 5/026 (2006.01)

(52) U.S. Cl.
CPC ........ *G01R 33/5635* (2013.01); *A61B 5/0044* (2013.01); *A61B 5/0263* (2013.01); *A61B 5/7275* (2013.01); *G01R 33/4828* (2013.01); *G01R 33/56308* (2013.01); *A61B 2576/023* (2013.01)

(58) Field of Classification Search
CPC ............ G01R 33/5635; G01R 33/4828; G01R 33/56308; A61B 5/0044; A61B 5/0263; A61B 5/7275; A61B 2576/023

USPC .................................................. 324/300–322
See application file for complete search history.

(56) References Cited

U.S. PATENT DOCUMENTS

| 6,331,116 | B1 * | 12/2001 | Kaufman | G06K 9/209 345/418 |
| 6,514,082 | B2 * | 2/2003 | Kaufman | G06K 9/209 345/418 |
| 7,148,887 | B2 * | 12/2006 | Kaufman | G06K 9/209 345/419 |

(Continued)

FOREIGN PATENT DOCUMENTS

| CN | 104305998 A | * | 1/2015 |
| JP | 2014210084 A | * | 11/2014 |

(Continued)

OTHER PUBLICATIONS

Falk E., Why Do Plaques Rupture, www.ncbi.nlm.nih.gov/pubmed/1424049, Dec. 1992.*

(Continued)

*Primary Examiner* — Patrick Assouad
*Assistant Examiner* — Sean Curtis
(74) *Attorney, Agent, or Firm* — Oblon, McClelland, Maier & Neustadt, L.L.P.

(57) ABSTRACT

In one embodiment, an image processing device includes memory circuitry configured to store a program; and processing circuitry configured, by executing the program, to extract an outer wall of a tubular structure by using a fat image obtained by a water/fat separation method of magnetic resonance imaging, and generate a tubular-structure wall image in which a wall of the tubular structure is distinguished, based on the outer wall.

16 Claims, 14 Drawing Sheets

(56) References Cited

U.S. PATENT DOCUMENTS

| | | | | |
|---|---|---|---|---|
| 7,194,117 B2* | 3/2007 | Kaufman | ................ | A61B 5/055 378/41 |
| 7,336,986 B2* | 2/2008 | Miyoshi | ............. | G01R 33/4828 128/898 |
| 7,473,843 B2* | 1/2009 | Wang | ................. | A61K 49/1818 174/36 |
| 7,474,776 B2* | 1/2009 | Kaufman | ............... | A61B 5/055 378/41 |
| 7,477,768 B2* | 1/2009 | Kaufman | .............. | G06T 7/0012 378/41 |
| 7,486,811 B2* | 2/2009 | Kaufman | .............. | G06T 7/0012 378/21 |
| 8,213,699 B2* | 7/2012 | Wakai | ................... | G06F 19/321 382/131 |
| 8,447,090 B2* | 5/2013 | Wakai | ................... | G06F 19/321 382/131 |
| 8,913,812 B2* | 12/2014 | Yokota | ................... | A61B 6/032 382/128 |
| 8,942,460 B2* | 1/2015 | Nakano | ................. | A61B 6/032 382/133 |
| 9,002,082 B2* | 4/2015 | Ambwani | ............ | G01R 33/481 382/128 |
| 9,141,763 B2* | 9/2015 | Sharma | ................ | G16H 50/50 |
| 9,196,057 B2* | 11/2015 | Wakai | ................... | A61B 6/5211 |
| 9,324,150 B2* | 4/2016 | Hautvast | ............. | G01R 33/543 |
| 9,449,387 B2* | 9/2016 | Wakai | ................... | A61B 6/5211 |
| 9,488,711 B2* | 11/2016 | Kimura | ................. | A61B 5/055 |
| 9,613,426 B2* | 4/2017 | Matthews | .............. | G06T 7/174 |
| 9,761,048 B2* | 9/2017 | Igarashi | ................. | G06T 19/00 |
| 9,835,707 B2* | 12/2017 | Yeo | ..................... | G01R 33/5607 |
| 10,043,267 B2* | 8/2018 | Yamamori | ............ | G06T 7/0012 |
| 10,052,033 B2* | 8/2018 | Bi | ...................... | A61B 5/02007 |
| 2004/0064035 A1* | 4/2004 | Miyoshi | ............. | G01R 33/4828 600/410 |
| 2007/0127804 A1* | 6/2007 | Yoshida | .................. | G06K 9/00 382/131 |
| 2008/0304616 A1* | 12/2008 | Van Uitert, Jr. | ...... | G06T 7/0012 378/4 |
| 2009/0326617 A1* | 12/2009 | Asano | ................ | A61B 5/02007 607/89 |
| 2010/0008557 A1* | 1/2010 | Matsumoto | ........ | G06K 9/00208 382/131 |
| 2010/0085052 A1* | 4/2010 | Johnson | ............. | G01R 33/4824 324/309 |
| 2010/0092053 A1* | 4/2010 | Manabe | ............... | G06K 9/4638 382/128 |
| 2012/0026162 A1* | 2/2012 | Masumoto | .............. | G06T 19/00 345/419 |
| 2012/0093388 A1* | 4/2012 | Masumoto | ............ | G06T 7/0012 382/134 |
| 2012/0207371 A1* | 8/2012 | Wakai | ................... | G06F 19/321 382/131 |
| 2012/0263368 A1* | 10/2012 | Nakano | .................. | A61B 6/032 382/133 |
| 2013/0315455 A1* | 11/2013 | Wakai | .................. | A61B 6/5211 382/128 |
| 2015/0193921 A1* | 7/2015 | Hautvast | .............. | G01R 33/543 382/131 |
| 2015/0310650 A1* | 10/2015 | Lu | ....................... | G01R 33/5608 324/322 |
| 2015/0356734 A1* | 12/2015 | Ooga | ....................... | A61B 6/03 382/131 |
| 2016/0061918 A1* | 3/2016 | Yeo | ....................... | G01R 33/243 324/309 |
| 2016/0071267 A1* | 3/2016 | Wakai | .................. | A61B 6/5211 382/128 |
| 2016/0078677 A1* | 3/2016 | Igarashi | ................ | G06T 7/0012 382/131 |
| 2017/0143853 A1* | 5/2017 | Maki | ....................... | A61B 5/418 |
| 2017/0227620 A1* | 8/2017 | Wakai | ................ | G01R 33/5635 |
| 2017/0307715 A1* | 10/2017 | Eggers | ............... | G01R 33/4828 |
| 2018/0020998 A1* | 1/2018 | Wakai | ................ | A61B 6/504 345/420 |
| 2018/0174297 A1* | 6/2018 | Ooga | ....................... | A61B 6/03 |

FOREIGN PATENT DOCUMENTS

| | | | | |
|---|---|---|---|---|
| JP | 2015-522374 | | 8/2015 | |
| JP | 2017140132 A | * | 8/2017 | ......... G01R 33/5635 |
| JP | 2017140132 A | * | 8/2017 | ......... G01R 33/5635 |

OTHER PUBLICATIONS

Falk E., Why Do Plaques Rupture, www.ncbi.nlm.nih.gov/pubmed/1424049, Dec. 1992. (Year: 1992).*

* cited by examiner

IMAGE PROCESSING DEVICE AND MRI APPARATUS

CROSS-REFERENCE TO RELATED APPLICATIONS

This application is based upon and claims the benefit of priority from Japanese Patent Application No. 2016-22378 filed on Feb. 9, 2016, the entire contents of which are incorporated herein by reference.

FIELD

Embodiments described herein relate generally to an image processing device and an MRI (Magnetic Resonance Imaging) apparatus.

BACKGROUND

Tissue characterization of a vessel wall and presence/absence of stenosis are determined on the basis of, e.g., a vessel shape obtained by analyzing an image imaged by a modality such as an X-ray CT (Computed Tomography) apparatus and an MRI apparatus.

However, in order to analyze a shape of a tubular structure such as a blood vessel or tissue characterization of a wall of a tubular structure such as a vessel wall, it is required that a wall of a tubular structure is accurately specified. In conventional technology, a blood flow inside an examinee is imaged by using a contrast agent, then an inner wall of a vessel (i.e., vascular inner periphery) is positionally identified from the imaged blood flow, and then a position of a vessel wall is analyzed by estimating an outer wall of a vessel (i.e., vascular outer periphery) based on the identified inner wall of a vessel.

DETAILED DESCRIPTION

In one embodiment, an image processing device includes memory circuitry configured to store a program; and processing circuitry configured, by executing the program, to extract an outer wall of a tubular structure by using a fat image obtained by a water/fat separation method of magnetic resonance imaging, and generate a tubular-structure wall image in which a wall of the tubular structure is distinguished, based on the outer wall.

Hereinafter, each embodiment of an image processing device and each embodiment of an MRI apparatus will be described with reference to the accompanying drawings. In the present specification, embodiments of image processing devices will be described as the first to fourth embodiments, and then an embodiment of an MRI apparatus will be described as the fifth embodiment. Note that the same reference numbers are assigned to the same components in each figure, and duplicate description is omitted.

First Embodiment

The first embodiment relates to a method of extracting a wall of a tubular structure based on a water/fat separated image of MRI.

Figure 1:
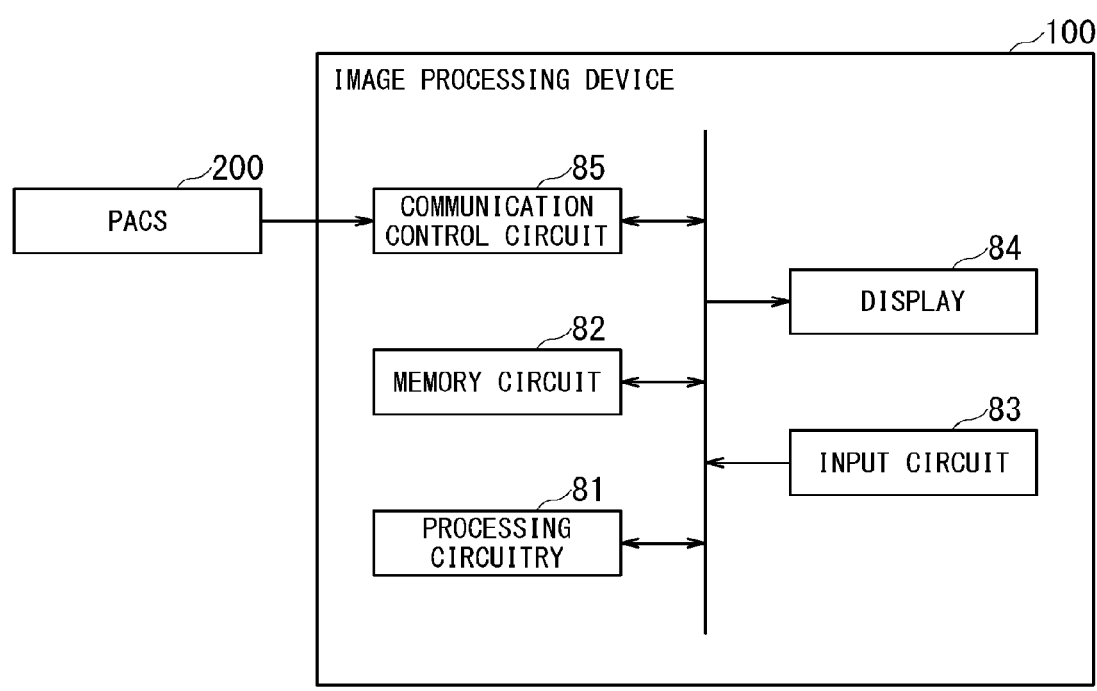
FIG. 1 is a block diagram illustrating overall configuration of the image processing device of the first embodiment.

FIG. 1 is a block diagram illustrating overall configuration of the image processing device 100 of the first embodiment. As shown in FIG. 1, the main structure of the image processing device 100 is configured as a computer, and the image processing device 100 can intercommunicate with an external device via a network such as a LAN (Local Area Network). The image processing device 100 includes, e.g., processing circuitry 81, a memory circuit 82, an input circuit 83, and a display 84 as hardware components. Additionally, the image processing device 100 is connected to a PACS (Picture Archiving and Communication Systems) 200 via an electronic network through the communication control circuit 85.

The communication control circuit 85 implements various communication protocols according to a network aspect. The above-described electronic network means a general information communication network using telecommunications technology and includes, e.g., a telephone communication network, an optical fiber communication network, a cable communication network, and a satellite communication network in addition to a hospital LAN (Local Area Network), a wireless/wired LAN, and the Internet network. The image processing device 100 acquires image data of medical images from the PACS 200 via the electronic network.

Incidentally, the PACS 200 and the image processing device 100 may be configured as a system of cloud computing.

The processing circuitry 81 may be configured of special-purpose hardware or be configured to implement various types of functions by causing its built-in processor to perform software processing. In the present embodiment, a description will be given of a case where the processing circuitry 81 implements various types of functions by software processing of its processor. The processing circuitry 81 implements respective functions described below by reading out programs stored in the memory circuit 82 or programs directly installed in the processing circuitry 81 and executing those programs.

The above-described term "processor" means, e.g., a circuit such as a special-purpose or general-purpose CPU (Central Processing Unit), a special-purpose or general-purpose GPU (Graphics Processing Unit), an ASIC (Application Specific Integrated Circuit), a programmable logic device, and an FPGA (Field Programmable Gate Array). The above-described programmable logic device includes, e.g., an SPLD (Simple Programmable Logic Device) and a CPLD (Complex Programmable Logic Device).

Additionally, the processing circuitry 81 may be configured of a single processor or be configured by combining plural processors being independent of each other. In the latter case, the image processing device 100 may be configured so that plural memory circuits 82 corresponding to respective processors are provided and each program executed by each processor is stored in the memory circuit 82 corresponding to this processor. Additionally or alternatively, one memory circuit 82 may collectively store all the programs corresponding to the plural processors of the processing circuitry 81.

The memory circuit 82 is configured of, e.g., a hard disc, an optical disc, and a semiconductor memory such as a RAM (Random Access Memory) and a flash memory. Additionally, the memory circuit 82 may be configured of a portable medium such as a USB (Universal Serial Bus) memory and a DVD (Digital Video Disk). The memory circuit 82 stores image data, data required for executing each program, and various types of programs (including an application program and an operating system) executed by the processing circuitry 81. Further, the memory circuit 82 may be equipped with a GUI (Graphical User Interface) via which various types of commands for controlling the operating system can be inputted from the input circuit 83.

The input circuit 83 includes plural input devices such as a pointing device and a keyboard, and receives commands inputted to these input devices. Specifically, when an operator manipulates the input devices, the input circuit 83 generates an input signal in accordance with the manipulation and outputs the generated input signal to the processing circuitry 81.

The display 84 is a display device such as a liquid crystal display panel, a plasma display panel, and an organic EL (Electro Luminescence) panel. The display 84 displays images under the control of the processing circuitry 81.

Figure 2:
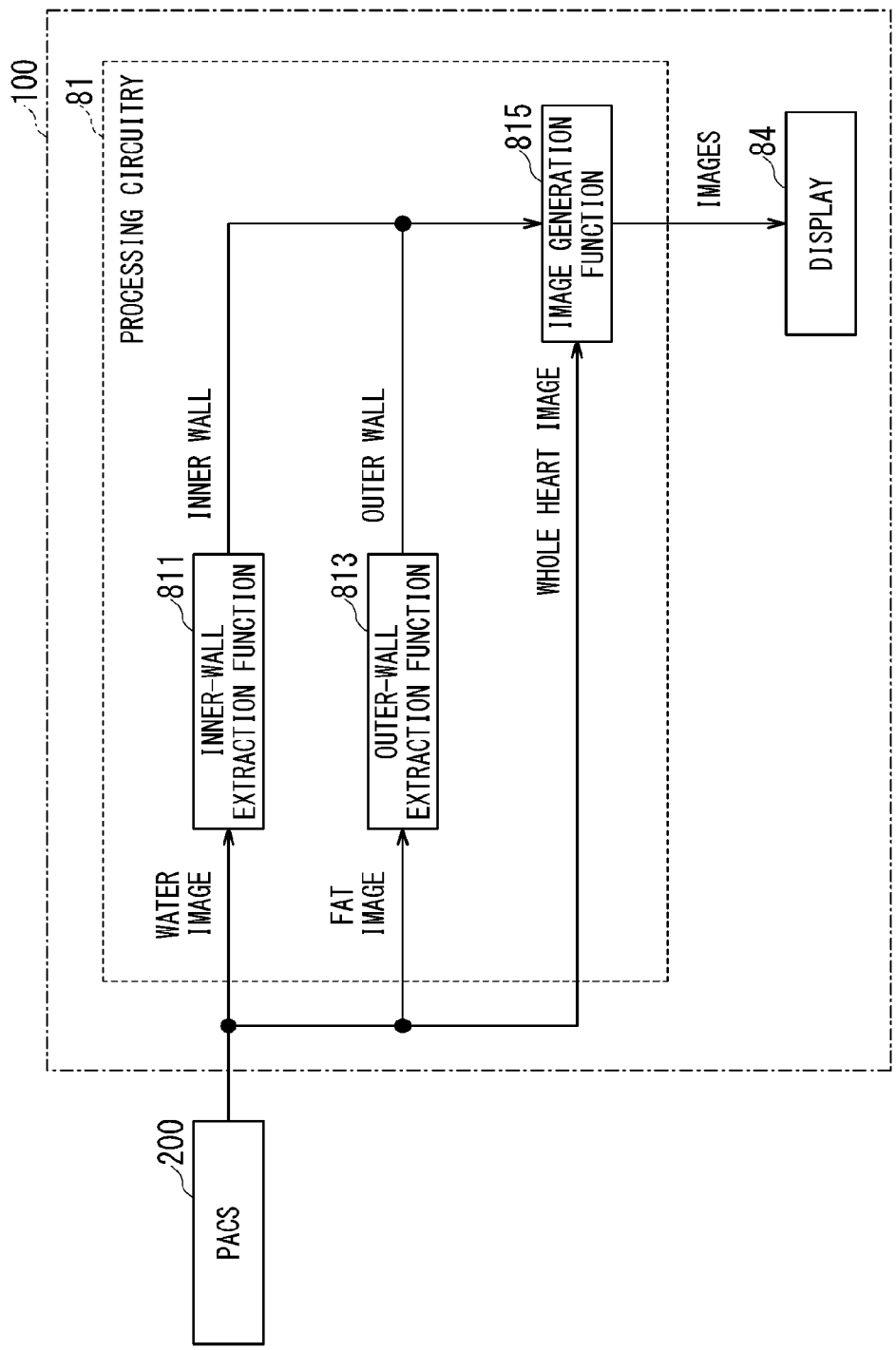
FIG. 2 is a functional block diagram illustrating detailed configuration of the processing circuitry in FIG. 1.

FIG. 2 is a functional block diagram illustrating detailed configuration of the processing circuitry 81 in FIG. 1. The processing circuitry 81 of the image processing device 100 implements an inner-wall extraction function 811, an outer-wall extraction function 813, and an image generation function 815, by reading out and executing the programs corresponding to those functions 813 to 815 stored in the memory circuit 82.

The inner-wall extraction function 811 is a function of extracting an inner wall of a tubular structure by using a water image obtained under the water/fat separation method of MRI. The method of extracting an inner wall of a tubular structure from a water image will be described below.

The outer-wall extraction function 813 is a function of extracting an outer wall of a tubular structure by using a fat image obtained under the water/fat separation method of MRI. The method of extracting an outer wall of a tubular structure from a fat image will be described below.

The image generation function 815 is a function of generating a tubular-structure wall image identified by an inner wall and an outer wall. Additionally, the image generation function 815 is also a function of generating, e.g., an image in which a tubular-structure wall image and a three-dimensional image including the entire heart such as a whole heart image are associated with each other.

Figure 3:
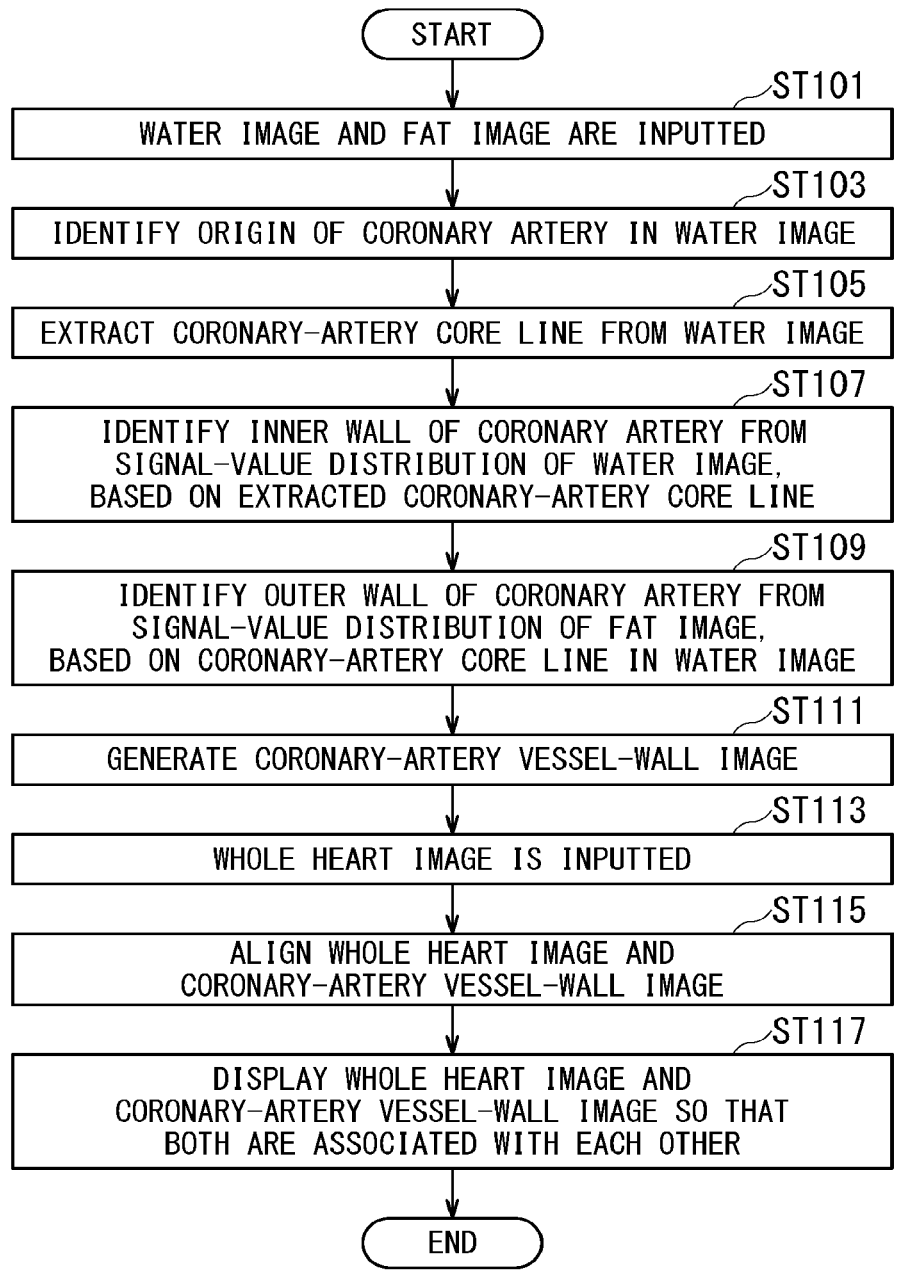
FIG. 3 is a flowchart illustrating an operation of the image processing device of the first embodiment.

FIG. 3 is a flowchart illustrating an operation of the image processing device 100 of the first embodiment. In the following, according to the step numbers in the flowchart shown in FIG. 3, an operation of the image processing device 100 will be described by referring to FIG. 4 to FIG. 6 as required. In the present embodiment, a description will be given of a case of a cardiac coronary artery as a tubular structure.

In the step ST101, a cardiac water image and a cardiac fat image in each of which the same region of the same object including a coronary artery is depicted are inputted from the PACS 200 to the image processing device 100.

Those water image and fat image are acquired by, e.g., computation based on an MR (Magnetic Resonance) image imaged under the Dixon method. Incidentally, those water image and fat image may be two-dimensional images or three-dimensional images.

The Dixon method is an imaging method using phase difference caused by difference in resonance frequency between protons of intravital water and protons of intravital fat. For instance, in an MRI apparatus in which a static magnetic field of 1.5 Tesla is applied, the difference in magnetic resonance frequency between protons of water and protons of fat is approximately 220 Hz. According to the above difference in magnetic resonance frequency, protons of water and protons of fat are in the same phase when the echo time TE is 0 msec (millisecond), are in opposite phase when the echo time TE is approximately 2.25 msec, and fall in the same phase again when the echo time TE is approximately 4.5 msec. On the basis of an in-phase image and an out-phase image (i.e., antiphase image) acquired in the above manner, each water image and each fat image are generated.

When a magnetic resonance signal emitted from protons of water is defined as Sw and a magnetic resonance signal emitted from protons of fat is defined as Sf, an in-phase image reflects a magnetic resonance signal indicated by Sw+Sf and an out-phase image reflects a magnetic resonance signal indicated by Sw−Sf. Each water image and each fat image are generated on the basis of such an in-phase image and an out-phase image.

A magnetic resonance signal emitted from each proton of water is detected with strong intensity in imaging of water images. Thus, in a cardiac water image in which a coronary artery is depicted, each blood region is distinguishably depicted as, e.g., a pixel region of high brightness. Contrastively, a magnetic resonance signal emitted from each proton of fat is detected with strong intensity in imaging of fat images, and each fat region is distinguishably depicted as, e.g., a pixel region of high brightness. Incidentally, the processing circuitry 81 may generate a water image by reversing brightness and darkness so that each blood region is distinguishably depicted as a pixel region of low brightness. The same holds true for a fat image.

Returning back to FIG. 3, the description of the flowchart is continued.

In the step ST103, the inner-wall extraction function 811 identifies an origin of a coronary artery in a water image. Identification of an origin of a coronary artery will be described in detail with reference to FIG. 4.

Figure 4:
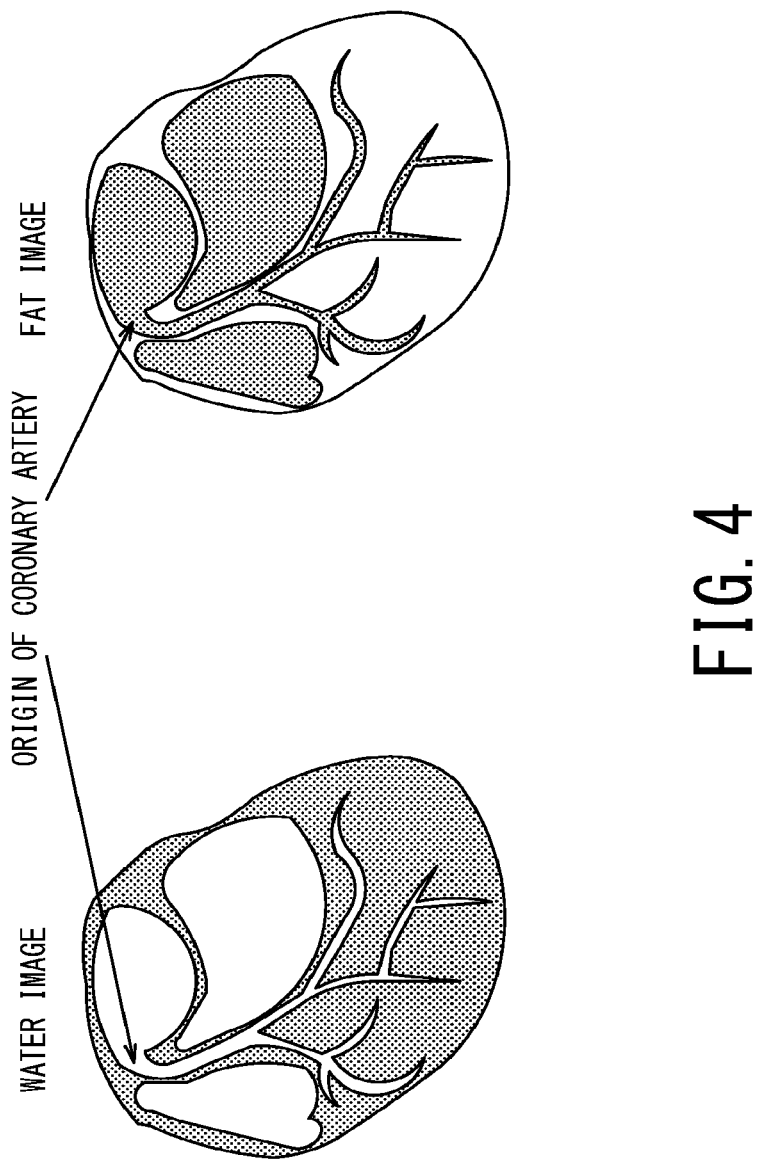
FIG. 4 is a schematic diagram illustrating a water image and a fat image in each of which an origin of a coronary artery is depicted.

FIG. 4 is a schematic diagram illustrating a water image and a fat image in each of which an origin of a coronary artery is depicted (included). The left side of FIG. 4 indicates a cardiac water image, and the right side of FIG. 4 indicates a cardiac fat image. As described above, a water image is an image in which blood is distinguishably depicted as, e.g., high brightness regions, and a fat image is an image in which each fat tissue is distinguishably depicted as, e.g., high brightness regions. In the case of FIG. 4, a region where magnetic-resonance-signal intensity in imaging is higher is whitely indicated, and a region where magnetic-resonance-signal intensity in imaging is lower is darkly indicated.

In each of the right and left sides of FIG. 4, the position indicated by the arrow is an origin of a coronary artery. An origin of a coronary artery indicates a root position from which a coronary artery extends. As described above, in order to identify the target blood vessel, the inner-wall extraction function 811 identifies the origin of the target blood vessel in the first step.

Here, template image data of a standard human model such as a shape of each organ, relative positional relationship between respective organs, arrangement of respective blood vessels, relative positional relationship between respective blood vessels, and a skeleton are stored in the memory circuit 82. The inner-wall extraction function 811 identifies an origin of a coronary artery by, e.g., extracting anatomical landmarks from each of a water image and a fat image based on pattern matching between the template image data and image data of those water image and fat image. As to methods of identifying an origin of a coronary artery, the same methods as conventional technology can be used and further description is omitted.

Additionally, the first embodiment is not limited to a case where the image processing device 100 automatically identifies an origin of a coronary artery. For instance, the processing circuitry 81 may cause the display 84 to display a water image and a fat image so that a user can designate an origin of a coronary artery via an input device and the subsequent processing is performed on the basis of an origin of a coronary artery manually inputted by a user.

Returning back to FIG. 3, the description of the flowchart is continued.

In the step ST105, the inner-wall extraction function 811 extracts a coronary-artery core line from a water image by using, e.g., the information as follows. Firstly, the root position of the coronary-artery core line in the water image determined by the origin of the coronary artery identified in the step ST103 can be used. Secondly, geometric positional information on an existence region of a coronary artery obtained by tracking down a distinguishably depicted blood regions in the water image from the root position according to the standard shape of a coronary artery included in the template image data can be used.

In the step ST107, the inner-wall extraction function 811 identifies a coronary-artery inner-wall from signal distribution (i.e., pixel-value distribution) of the water image, on the basis of the extracted coronary-artery core line.

In the step ST109, the outer-wall extraction function 813 identifies a coronary-artery outer-wall from signal distribution (i.e., pixel-value distribution) of the fat image, on the basis of the extracted coronary-artery core line.

Figure 5:
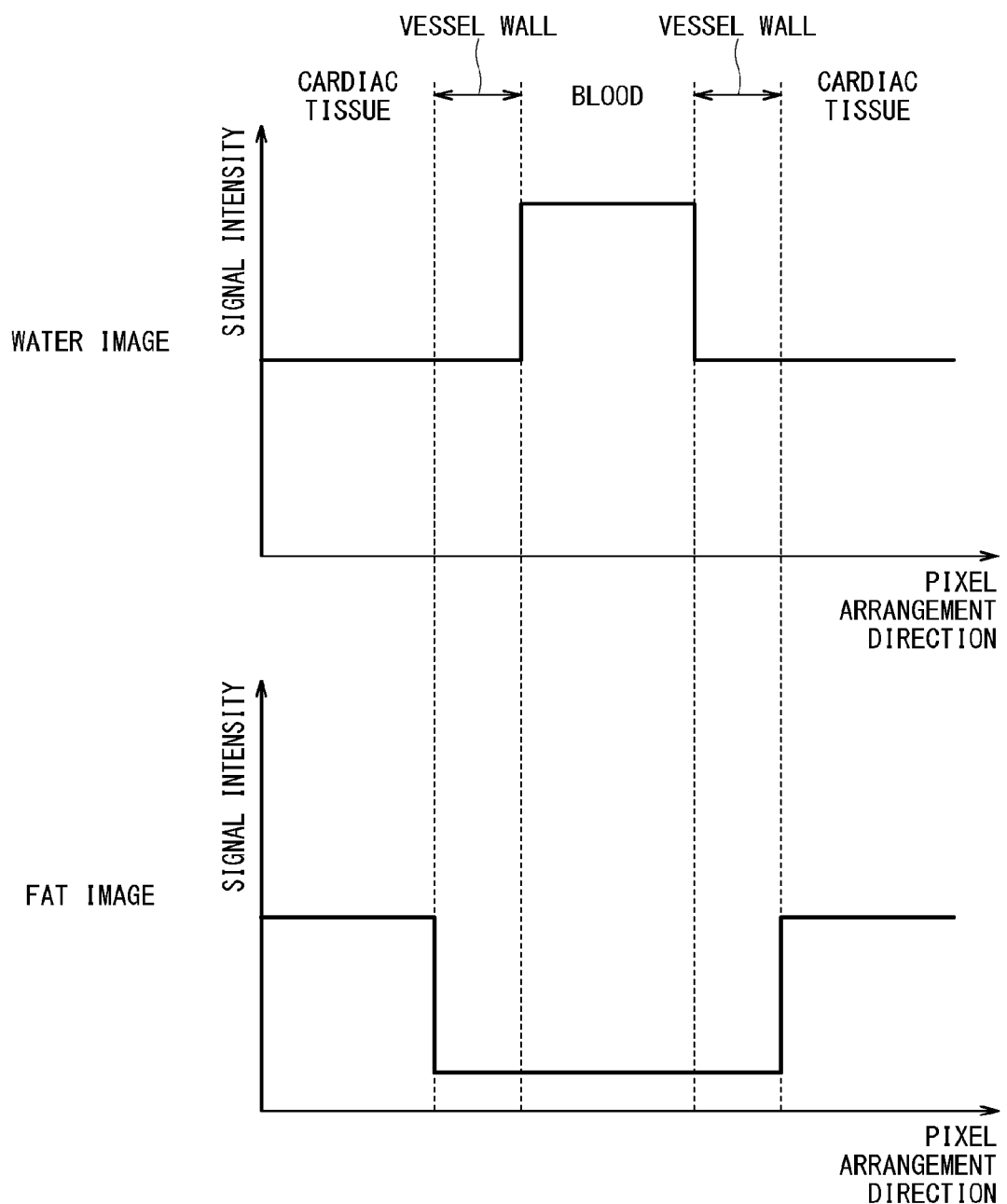
FIG. 5 is a schematic graph illustrating intensity distribution of magnetic resonance signals around a blood vessel in each of a water image and a fat image.

FIG. 5 is a schematic graph illustrating intensity distribution of magnetic resonance signals around a blood vessel in each of a water image and a fat image. The upper part of FIG. 5 is a graph in which intensity distribution of magnetic resonance signals around blood vessels in a water image is plotted for each pixel. The lower part of FIG. 5 is a graph in which intensity distribution of magnetic resonance signals around blood vessels in a fat image is plotted for each pixel. In each of the upper and lower parts of FIG. 5, the vertical axis indicates signal intensity of a magnetic resonance signal from a position corresponding to each pixel, and the horizontal axis indicates a pixel arrangement direction. When image data of each water image and each fat image are generated so that a region with stronger intensity of a magnetic resonance signal has a larger pixel value, the vertical axis may be interpreted as a pixel value.

In an image around a coronary artery, various tissues surrounding the coronary artery as well as the coronary artery are depicted. For instance, in each graph around the coronary artery in FIG. 5, tissues are assumed to be arranged in the order of a cardiac tissue, a vessel wall, blood (i.e., a lumen of a coronary artery), a vessel wall, and a cardiac tissue from left to right.

A water image is an image generated by detecting magnetic resonance signals from blood regions with strong intensity. Thus, in the signal intensity distribution shown in the upper part of FIG. 5, signal intensity is strong in the central part, i.e., the region corresponding to a lumen of a coronary artery filled with blood.

Contrastively, a fat image is an image generated by detecting magnetic resonance signals from each tissue and each organ including fat. Thus, in the signal intensity distribution shown in the lower part of FIG. 5, signal intensity is strong in the regions of both ends where cardiac tissues exist.

The four vertical broken lines in the upper and lower parts of FIG. 5 indicate border lines at which signal distribution largely changes in each of the water image and the fat image. The two interior broken lines are border lines indicating that the region sandwiched between them in the water image is strong in magnetic-resonance-signal intensity. The two exterior broken lines are border lines at which magnetic-resonance-signal intensity largely changes so that the region sandwiched between them in the fat image is weak in magnetic-resonance-signal intensity. According to the signal distribution in the water image and the fat image, a coronary-artery vessel-wall exists in each section sandwiched between the two interior or exterior broken lines.

As described above, in an image around a coronary artery, tissues are arranged in the order of a cardiac tissue, a vessel wall, blood (i.e., a lumen of coronary artery), a vessel wall, and a cardiac tissue. The section sandwiched between the two interior broken lines indicates blood (i.e., a lumen of a coronary artery), and each of the two sections from each of the two exterior broken lines to either end of the graph indicates a cardiac tissue. In other words, a coronary-artery vessel-wall exists in the two sections each of which is sandwiched between the border line of signal intensity on the right or left side in the water image and the border line of signal intensity on the right or left side in the fat image.

Figure 6:
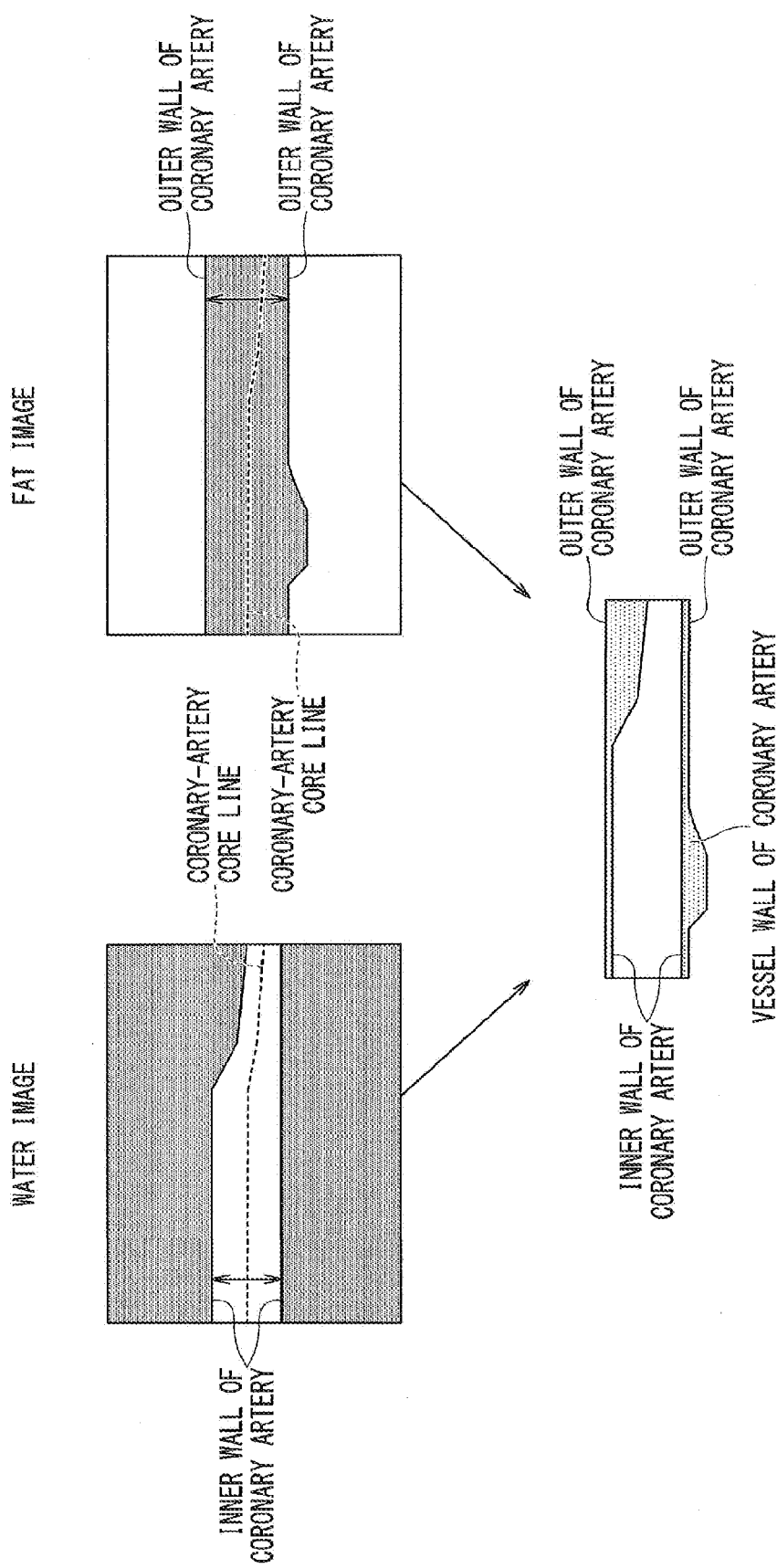
FIG. 6 is a conceptual diagram illustrating a vessel wall of a coronary artery identified from signal distribution in each of a water image and a fat image.

FIG. 6 is a conceptual diagram illustrating a vessel wall of a coronary artery identified from signal distribution in each of a water image and a fat image. The upper left part of FIG. 6 is a part of the cardiac water image shown in FIG. 4, and is an image indicating the periphery of the coronary artery. Similarly, the upper right part of FIG. 6 is a part of the cardiac fat image shown in FIG. 4, and is an image indicating the periphery of the coronary artery.

As shown in the upper left part of FIG. 6, the inner-wall extraction function 811 extracts a coronary-artery core line in the water image, and identifies a coronary-artery inner-wall from signal distribution based on the extracted coronary-artery core line. As described in the graph of FIG. 5, the inner-wall extraction function 811 identifies the boundary plane in the water image between the region with strong magnetic-resonance-signal intensity and the regions with weak magnetic-resonance-signal intensity, i.e., the boundary plane around which pixel values largely change, as a coronary-artery inner-wall. The boundary plane between a region indicative of a high-level signal and a region indicative of a low-level signal is determined on the basis of, e.g., one or plural threshold values.

Similarly, as shown in the upper right part of FIG. 6, the outer-wall extraction function 813 identifies a coronary-artery outer-wall from signal distribution of the fat image based on the coronary-artery core line in the water image. In other words, the outer-wall extraction function 813 identifies the boundary plane in the fat image between the regions with strong magnetic-resonance-signal intensity and the region with weak magnetic-resonance-signal intensity, as a coronary-artery outer-wall.

Although a description has been given of a case where a coronary-artery core line of a water image is used for a coronary-artery core line of a fat image without change, a coronary-artery core line may be extracted in each of a water image and a fat image.

As described above, a structure (contour) of a coronary-artery vessel-wall as shown in the lower part of FIG. 6 is determined on the basis of a coronary-artery inner-wall and a coronary-artery outer-wall respectively identified from a water image and a fat image.

Returning back to FIG. 3, the description of the flowchart is continued.

In the step ST111, the image generation function 815 generates a coronary-artery vessel-wall image based on a coronary-artery inner-wall identified from a water image and a coronary-artery outer-wall identified from a fat image. A coronary-artery vessel-wall image is an image indicative of, e.g., a structure of a coronary-artery vessel-wall like the lower part of FIG. 6. In the coronary-artery vessel-wall image shown in the lower part of FIG. 6, prominent parts at which the vessel wall protrudes inward and/or outward are observed. As described above, a coronary-artery vessel-wall image is an image indicative of a contour of a vessel wall.

In the step ST113, a whole heart image is inputted from the PACS 200 to the image processing device 100. A whole heart image is a three-dimensional image in which blood vessels connected to a heart such as a coronary artery and an aorta as well as the entirety of a heart are depicted. A whole heart image is also an image by which the entirety of a heart can be observed from a bird's eye perspective. Such a whole heart image is an image obtained under electrocardiographic synchronization imaging or respiration-synchronized imaging in MRI.

As to a whole heart image, it is not limited to an MR image. Any three-dimensional image by which a structure of the entirety of a heart including its surrounding blood vessels can be observed from a bird's eye perspective may be used for a whole heart image. For instance, a CT image may be used for a whole heart image.

In the step ST115, the image generation function 815 align the whole heart image acquired in the step ST113 and the coronary-artery vessel-wall image generated in the step ST111. The coronary-artery vessel-wall image includes the same coronary-artery core line as the coronary-artery core line extracted from the water image or the fat image. Thus, the alignment may be performed on the basis of the coronary-artery core line or another known technique.

In the step ST117, the display 84 displays the whole heart image and the coronary-artery vessel-wall image so that the whole heart image and the coronary-artery vessel-wall image are associated with each other.

The foregoing is the description of the flowchart shown in FIG. 3.

Figure 7:
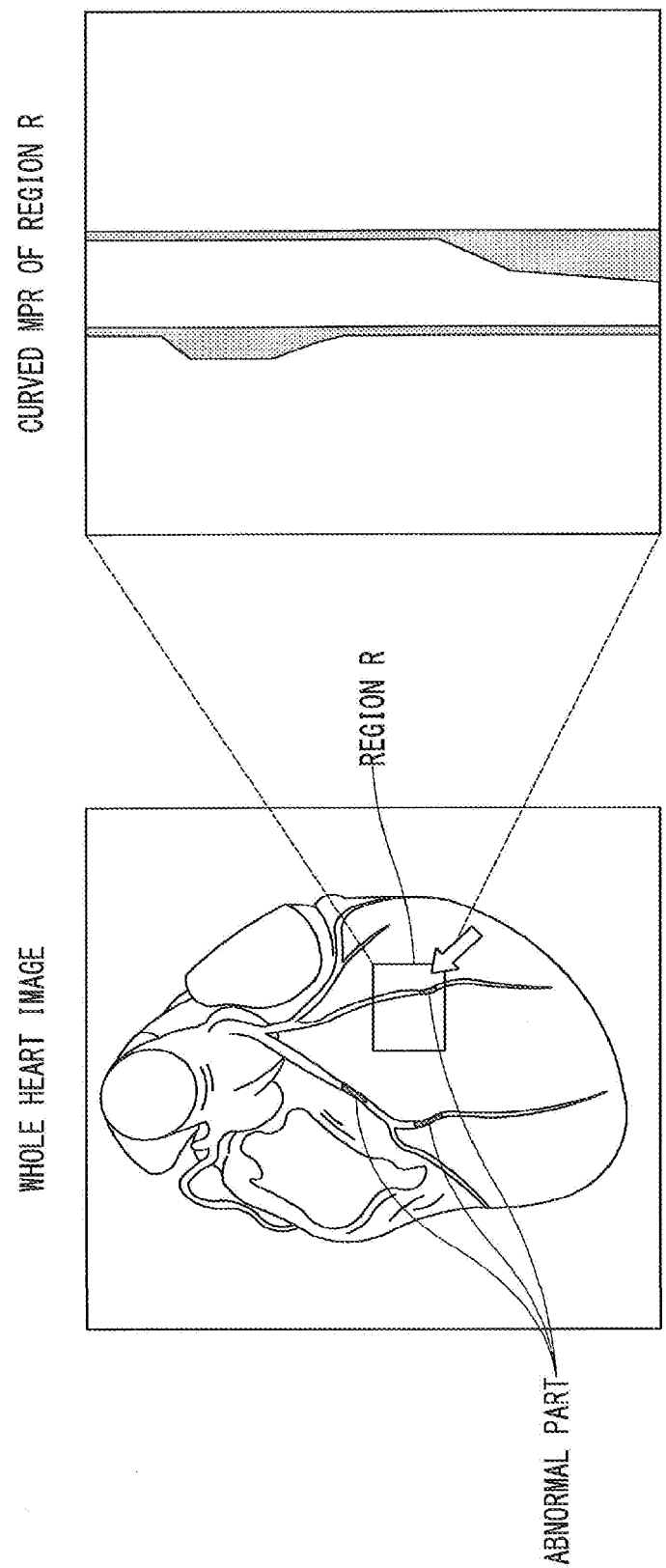
FIG. 7 is a schematic diagram illustrating an image to be displayed according to the image processing device of the first embodiment.

FIG. 7 is a schematic diagram illustrating an image to be displayed according to the image processing device 100 of the first embodiment. The left side of FIG. 7 indicates a whole heart image. The right side of FIG. 7 indicates curved MPR (Multi-Planar Reconstruction) in the region R of the whole heart image on the left side. The curved MPR on the right side of FIG. 7 is an instance of a coronary-artery vessel-wall image.

When a specific region in the whole heart image is selected under a condition where the whole heart image and the coronary-artery vessel-wall image are aligned with each other, the coronary-artery vessel-wall image corresponding to the selected region is displayed.

The abnormal regions filled with black in the whole heart image indicate parts where abnormality such as stenosis is observed in the whole heart image. For instance, a user can select one of abnormal regions from an image by which the entire heart can be observed from a bird's eye perspective like a whole heart image, as a region to be subjected to further analysis. By displaying the coronary-artery vessel-wall image corresponding to the selected region, a user can accurately determine whether the selected region is really a lesion or not, and thus can accurately determine which part should be cured.

Additionally, the processing circuitry 81 may identify a lesion such as a stenosis part by analyzing a coronary-artery vessel-wall image. Furthermore, the image generation function 815 may cause the display 84 to display a whole heart image in which the identified lesion area is emphasized, by assigning a chromatic color different from a color of its surrounding region or a normal region to the lesion area. Additionally or alternatively, the image generation function 815 may cause the display 84 to display a whole heart image in which the identified lesion area is distinguished, by superimposing a mark on the lesion area. For instance, the abnormal parts filled with black in the whole heart image shown on the left side of FIG. 7 may correspond to the identified lesion areas obtained by analyzing a coronary-artery vessel-wall image.

As described above, according to the image processing device 100 of the first embodiment, information obtained from a coronary-artery vessel-wall image is displayed together with a whole heart image by which the entire heart can be observed from a bird's eye perspective. Thus, a user can easily and quickly obtain information on a lesion area.

Although a description has been given of a case where alignment is performed on the basis of a generated coronary-artery vessel-wall image in the image processing device 100 of the first embodiment, embodiments of the present disclosure are not limited to such an aspect. For instance, a whole heart image may be inputted to the image processing device 100 in the step ST101 in addition to a water image and a fat image, and alignment between the inputted whole heart image and the water image or the fat image may be performed before extraction of an inner wall and an outer wall.

Additionally, a timing of extracting a coronary-artery vessel-wall is not limited to the timing described in the flowchart of FIG. 3. In other words, extraction of a coronary-artery vessel-wall may be performed after a region where abnormality such as stenosis is observed in a whole heart image is selected by a user.

Furthermore, extraction of a coronary-artery vessel-wall is not needed to be performed for all the regions. In other words, extraction of a coronary-artery vessel-wall may be performed on the basis of a region selected by a user in a water image and a fat image.

In the first embodiment, a description has been given of a case where two images, i.e., a water image and a fat image are used for identifying a wall of a tubular structure. However, a method of identifying a wall of a tubular structure is not limited to the above-described method. In other words, a wall of a tubular structure can be identified only from a fat image.

For instance, a vascular outer wall can be clearly depicted by superimposing a vascular outer wall extracted by the outer-wall extraction function 813 on a whole heart image. For instance, in the case of observing a blood vessel from an outer wall side like an open abdominal surgery, to be able to understand a shape of an outer wall is useful for planning a surgical operation.

Although a description has been given of a case where an image of a wall of a tubular structure is generated on the basis of a vascular inner wall extracted by a water image obtained under the water/fat separation method of MRI, an image used for extracting a vascular inner wall is not limited to the above-described case.

Plural methods for identifying a vascular inner wall have been established in conventional technology. For instance, a PC (Phase contrast) method and a TOF (Time of flight) method are non-contrast angiography of MRI. Each of the PC method and the TOF method is a technique of depicting a vascular inner wall by using change in amplitude and phase of MR signals from a moving object such as flowing blood.

Incidentally, a vascular inner wall may be extracted from an contrast-enhanced MR image or be extracted from an image imaged by a modality except an MRI apparatus. The image processing device 100 may be configured so that an image of a wall of a tubular structure is generated on the basis of such an inner wall extracted by a method except the water/fat separation method and an outer wall extracted from a fat image.

Second Embodiment

The second embodiment relates to a method of analyzing tissue characterization of a vessel wall in addition to the method of extracting a coronary-artery vessel-wall described in the first embodiment.

Figure 8:
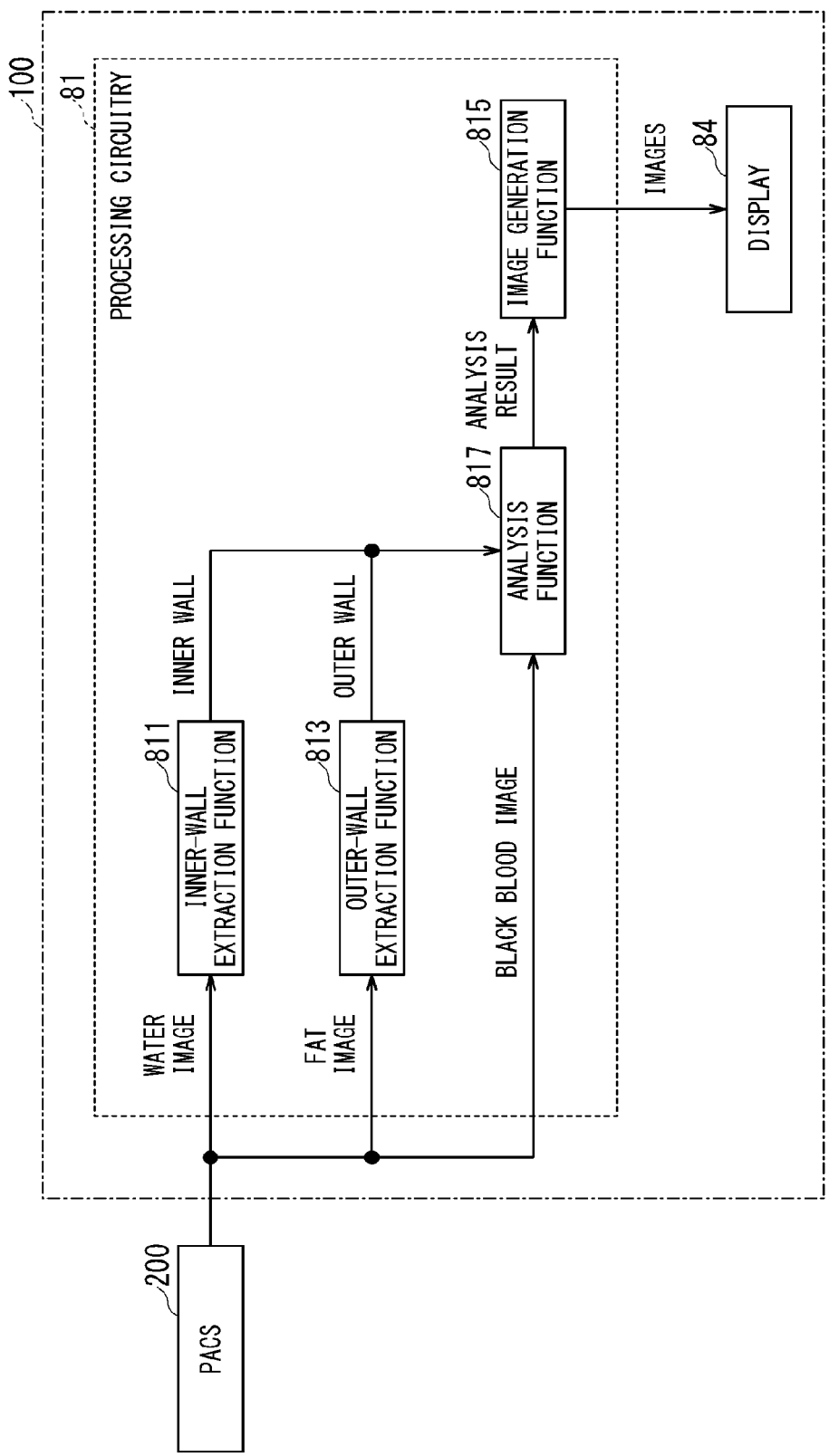
FIG. 8 is a block diagram illustrating functional configuration of the image processing device of the second embodiment.

FIG. 8 is a block diagram illustrating functional configuration of the image processing device 100 of the second embodiment. In FIG. 8, the processing circuitry 81 of the image processing device 100 in the second embodiment further implements an analysis function 817 in addition to the respective functions of the processing circuitry 81 of the image processing device 100 in the first embodiment shown in FIG. 2. The analysis function 817 is a function implemented by the processing circuitry 81 when the processing circuitry 81 executes the program corresponding to the analysis function 817 stored in the memory circuit 82.

The analysis function 817 analyzes tissue characterization of a coronary-artery vessel-wall so as to generate data of the analysis result. The analysis of tissue characterization of a coronary-artery vessel-wall includes analysis of tissue distribution of a coronary-artery vessel-wall, identification of a plaque existing in a coronary-artery vessel-wall, and analysis of various types of information such as nature of a tissue, a type of tissue, and planar dimension or cubic volume of a plaque.

In analysis of tissue distribution of a coronary-artery vessel-wall, e.g., a coronary-artery vessel-wall is divided into plural regions based on difference in magnetic-resonance-signal intensity, i.e., difference in pixel value, and tissue characterization of each of the plural regions is determined. For instance, tissue characterization of each of the plural regions is determined as one of normal, fibrosis, fat accumulation, and calcification.

In such analysis of tissue characterization of a coronary-artery vessel-wall, e.g., an MR image such as a Black Blood image and a T2 image is used. By aligning a coronary-artery vessel-wall image and another MR image such as a Black Blood image and a T2 image, analysis of tissue distribution and nature of a plaque is performed on the basis of a Black Blood image and/or a T2 image in which a coronary-artery vessel-wall is clearly identified.

Figure 9:
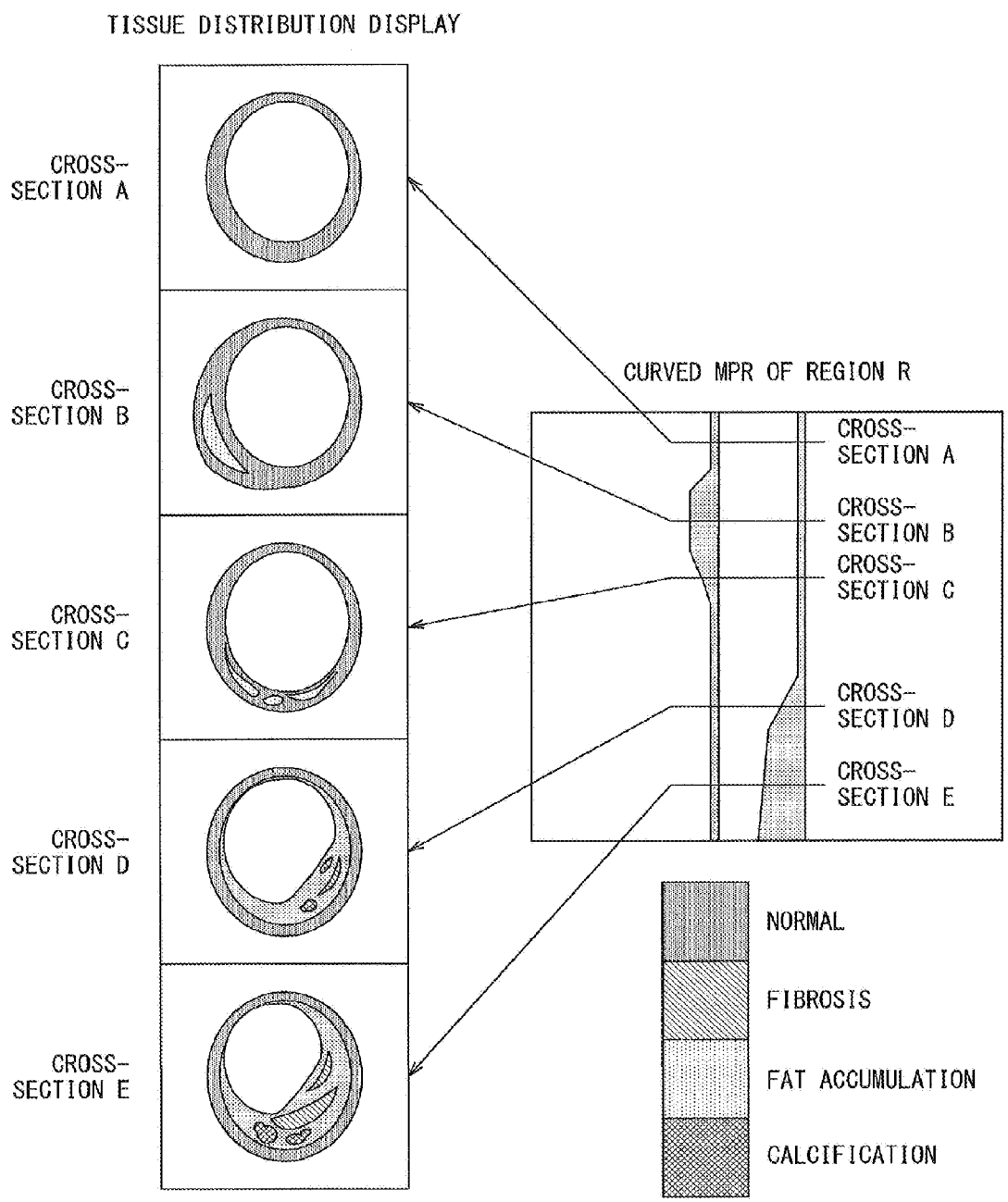
FIG. 9 is a schematic diagram illustrating an image to be displayed according to the image processing device of the second embodiment.

FIG. 9 is a schematic diagram illustrating an image to be displayed according to the image processing device 100 of the second embodiment. The right side of FIG. 9 is a coronary-artery vessel-wall image displayed on the basis of the curved MPR of the region R shown in FIG. 7. The left side of FIG. 9 indicates five cross-sectional images respectively corresponding to the cross-sections A, B, C, D, and E in the Curved MPR of the region R, as tissue distribution display. The bottom part of FIG. 9 shows legends of tissue distribution display, and indicates normal, fibrosis, fat accumulation, and calcification from the left in order. In the following description, the upper part of curved MPR of the region R in FIG. 9 is assumed to be the upstream side of the coronary artery.

The cross-section A on the left side of FIG. 9 is tissue distribution display of the coronary-artery vessel-wall of the cross-section at the most upstream side of the coronary artery in the curved MPR of the region R. In the cross-section A, any thickened part and/or prominent part is not observed in the structure of the coronary-artery vessel-wall indicated by the curved MPR of the region R. In the tissue distribution display of the cross-section a shown on the left side of FIG. 9, only normal tissues are observed.

In the cross-section B on the downstream side of the cross-section A, a thickened part protruding outward is observed on the left side of the coronary-artery vessel-wall shown by the curved MPR of the region R. In the tissue distribution of the cross-section B, fat accumulation is observed in the thickened part of the coronary-artery vessel-wall.

In the cross-section C on the further downstream side, a thickened part smaller than the thickened part in the cross-section B is observed on the left side of the coronary-artery vessel-wall shown by the curved MPR of the region R. In the tissue distribution of the cross-section C, a region in which fat is partially accumulated is observed.

In the cross-section D on the downstream side of the cross-section C, a thickened part protruding inward (i.e., toward the intravascular lumen side) is observed on the right side of the coronary-artery vessel-wall, which is different from the cross-sections B and C. In the tissue distribution of the cross-section D, a calcified part and a fibrosis part are observed in addition to a fat accumulation part.

In the cross-section E on the further downstream side of the cross-section D, a hyperplastic part more thickened than the thickened part in the cross-section D is observed on the right side of the coronary-artery vessel-wall. In the tissue distribution of the cross-section E, a calcified part and a fibrosis part which are larger than those in the cross-section D are observed.

As shown in FIG. 9, by displaying images as a result of analyzing tissue characterization of an arbitrary vascular cross-section, a user can easily obtain information on detailed tissue characterization of an abnormal part in a structure of a coronary-artery vessel-wall.

Additionally, tissue characterization of the entire coronary-artery vessel-wall can be analyzed by displaying cross-sections at predetermined intervals from the upstream side to the downstream side in the curved MPR of the region R. The cross-sections being set at predetermined intervals may be displayed in parallel or be displayed in motion. Moreover, the analyzed tissue characterization may be superimposed on the coronary-artery vessel-wall image to be displayed.

Furthermore, nature and a type of a plaque may be determined on the basis of the above-described tissue characterization. Additionally, planar dimension and/or cubic volume of a plaque, a calcified part and a fat accumulation part may be calculated.

As described above, according to the second embodiment, tissue characterization of a tissue wall of a coronary artery can be displayed in addition to displaying a structure of a tissue wall of a coronary artery. Thus, a user can obtain more detailed analysis results in which tissue characterization of a tissue wall of a coronary artery is added.

In the second embodiment, a method of analyzing tissue characterization of a vessel wall between an inner wall and a vascular outer wall has been described. However, characterization analysis of a vessel wall is not limited to the above-described method. In other words, tissue characterization of a vessel wall can be analyzed based solely on information on a vascular outer wall. For instance, if a position of a vascular outer wall is specified, tissue characterization of a vessel wall can be analyzed by analyzing tissue characterization of inside of a region surrounded by the specified vascular outer wall without information on a vascular inner wall.

Additionally, a position of a vascular inner wall can be estimated from tissue distribution obtained by analyzing characterization of a tissue existing in a region inside a vascular outer wall in a manner similar to the second embodiment.

Third Embodiment

The third embodiment relates to a method of analyzing a risk of plaque rupture based on plural water/fat separated images time-sequentially imaged under MRI using a result of time-sequential analysis of a structure of a vessel wall. The analysis of plaque rupture risk in the third embodiment is implemented by, e.g., the analysis function 817 shown in the block diagram of FIG. 8.

Figure 10:
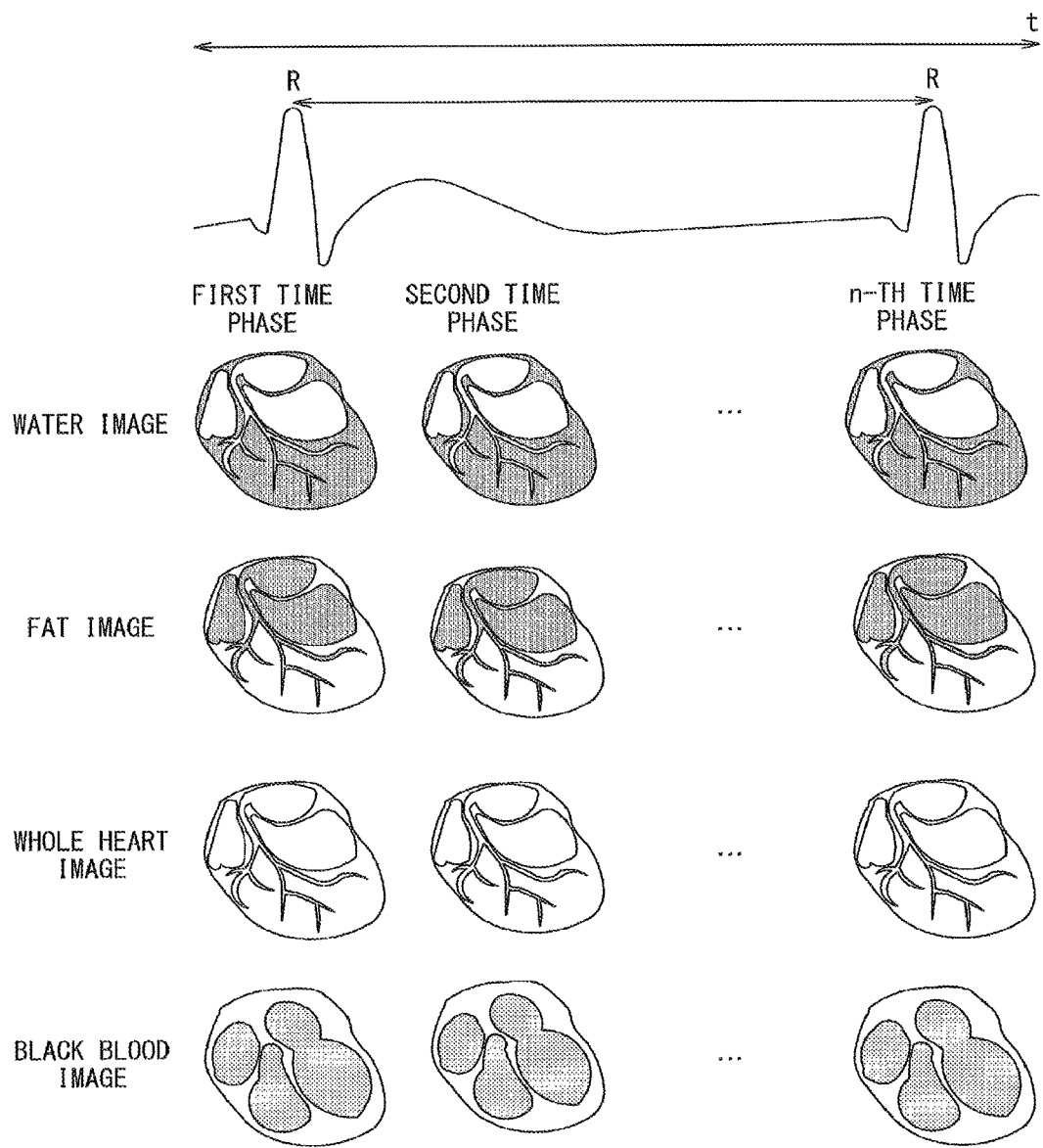
FIG. 10 is a schematic timing chart illustrating time-sequentially acquired image data in the image processing device of the third embodiment.

FIG. 10 is a schematic timing chart illustrating time-sequentially acquired image data in the image processing device 100 of the third embodiment. In FIG. 10, respective image data acquired in the first time phase, the second time phase, . . . , and the n-th time phase from the left are indicated. The respective image data shown in FIG. 10 indicate a water image of a water/fat separation image, a fat image of a water/fat separation image, a whole heart image, and a Black Blood image from the top.

For instance, when the structure of the coronary-artery vessel-wall described in the first embodiment is displayed together with whole heart images over plural time phases, water images of plural time phases, fat images of plural time phases, and whole heart images of plural time phases are inputted to the image processing device 100.

Additionally, when tissue characterization of the coronary-artery vessel-wall described in the second embodiment is analyzed over plural time phases, Black Blood images of plural time phases or non-illustrated T2 weighted images of plural time phases are inputted to the image processing device 100 in addition to water images of plural time phases and fat images of plural time phases.

Furthermore, coronary-artery vessel-wall images of plural time phases are generated from water images of plural time phases and fat images of plural time phases. A shape of a coronary-artery vessel-wall which temporally changes can be time-sequentially analyzed on the basis of those coronary-artery vessel-wall images of the respective time phases. By analyzing shape change of a coronary-artery vessel-wall in the above manner, for instance, risk of plaque rupture can be analyzed.

Figure 11A:
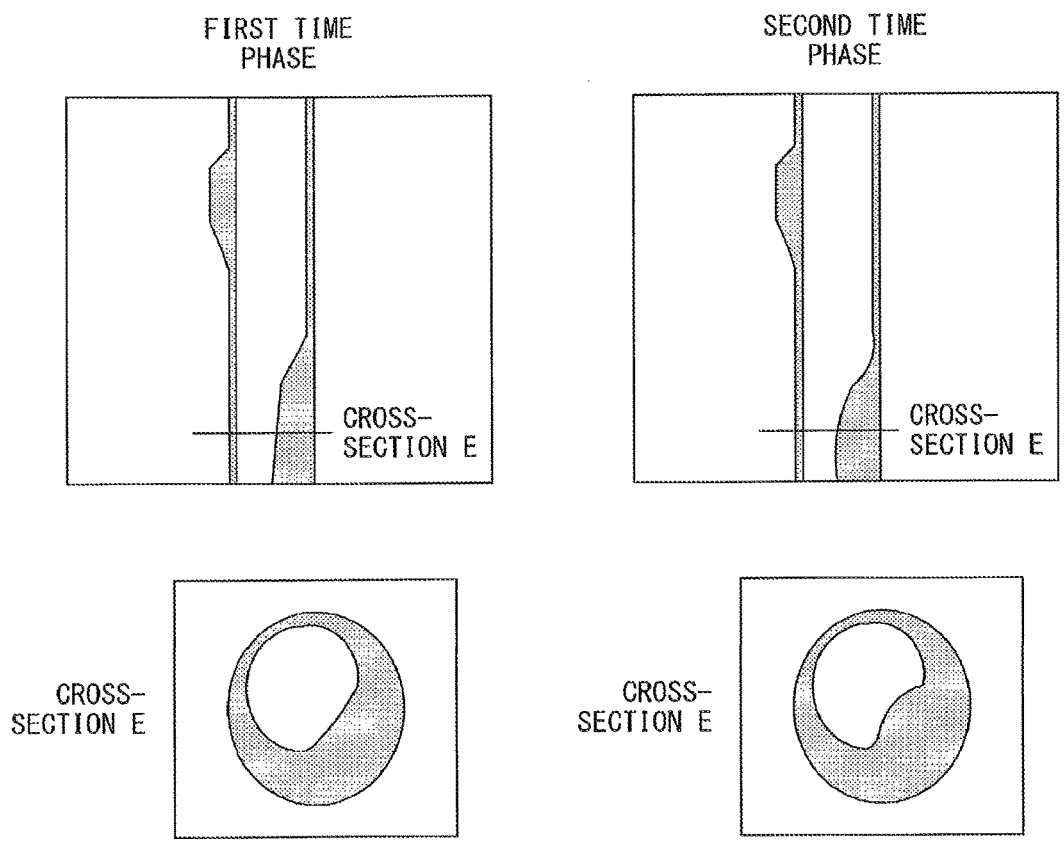
FIG. 11A is a schematic diagram of a coronary-artery vessel-wall image in each of the first time phase and the second time phase.
Figure 11B:
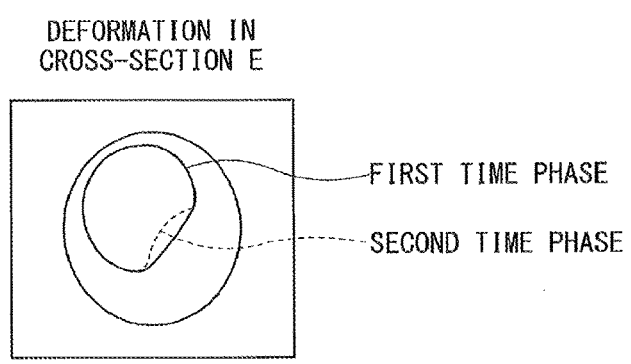
FIG. 11B is a conceptual diagram illustrating a method of calculating deformation volume of a vessel wall according to the image processing device of the third embodiment.

FIG. 11A and FIG. 11B are conceptual diagrams illustrating a method of calculating deformation volume of a vessel wall according to the image processing device 100 of the third embodiment. The upper left part of FIG. 11A indicates a coronary-artery vessel-wall image of the first time phase, and the lower left part of FIG. 11A is a cross-sectional diagram corresponding to the cross-section E shown in the upper left part of FIG. 11A. Similarly, the upper right part of FIG. 11A indicates a coronary-artery vessel-wall image of the second time phase, and the lower right part of FIG. 11A is a cross-sectional diagram corresponding to the cross-section E shown in the upper right part of FIG. 11A. A plaque exists at the cross-section E of the coronary-artery vessel-wall shown in FIG. 11A, and the coronary-artery vessel-wall is stenosed.

As is clear from comparison between the upper left part and the upper right part in FIG. 11A, the structure of the coronary-artery vessel-wall around the cross-section E is deformed so as to protrude toward the intravascular lumen in the second time phase, as compared with the first time phase. This deformation is also recognizable from comparison between the lower left part and the lower right part in FIG. 11A.

FIG. 11B is a superimposed image of the two images of the first and second time phases shown in the lower part of FIG. 11A. In FIG. 11B, the coronary-artery vessel-wall in the first time phase is indicated by a solid line, and the coronary-artery vessel-wall in the second time phase is indicated by a broken line. As shown in FIG. 11B, the structure of the coronary-artery vessel-wall is deformed so as to protrude toward the intravascular lumen in the second time phase, as compared with the first time phase.

Deformation volume may be calculated as, e.g., difference in sectional area or volume in a cross-sectional diagram. Additionally, deformation volume may be calculated on the basis of a vector indicating deformation of a coronary-artery vessel-wall.

As shown in FIG. 11B, risk of rupture for a plaque existing in a coronary-artery vessel-wall can be determined by time-sequentially analyzing deformation volume of this coronary-artery vessel-wall depicted in a coronary-artery vessel-wall image. Analysis of plaque rupture risk is performed on the basis of tissue distribution described in the second embodiment, information on a plaque such as its type, and deformation volume of a plaque determined from a composite image like FIG. 11B.

For instance, a plaque with a great amount of fat accumulation has a tendency to easily rupture. Contrastively, a fibrotic or calcified plaque has a tendency to hardly rupture, and has a lower risk of rupturing due to deformation as compared with a plaque including a great amount of fat.

Incidentally, when image data are time-sequentially analyzed, a more accurate analysis result is obtained from image data acquired at shorter intervals. In the case of a cardiac analysis, it is preferable to acquire image data of plural images in each period of one cardiac beat, i.e., acquire image data of plural time phases for each cardiac beat period based on an R-R interval. As compared with imaging with the use of an X-ray CT apparatus, imaging with the use of an MRI apparatus is advantageous in that there is no risk of X-ray exposure. Hence, in the case of using an MRI apparatus, image data of more time phases can be acquired in each cardiac beat period and thus more accurate analysis of plaque rupture risk can be achieved as compared with the case of using an X-ray CT apparatus.

Figure 12:
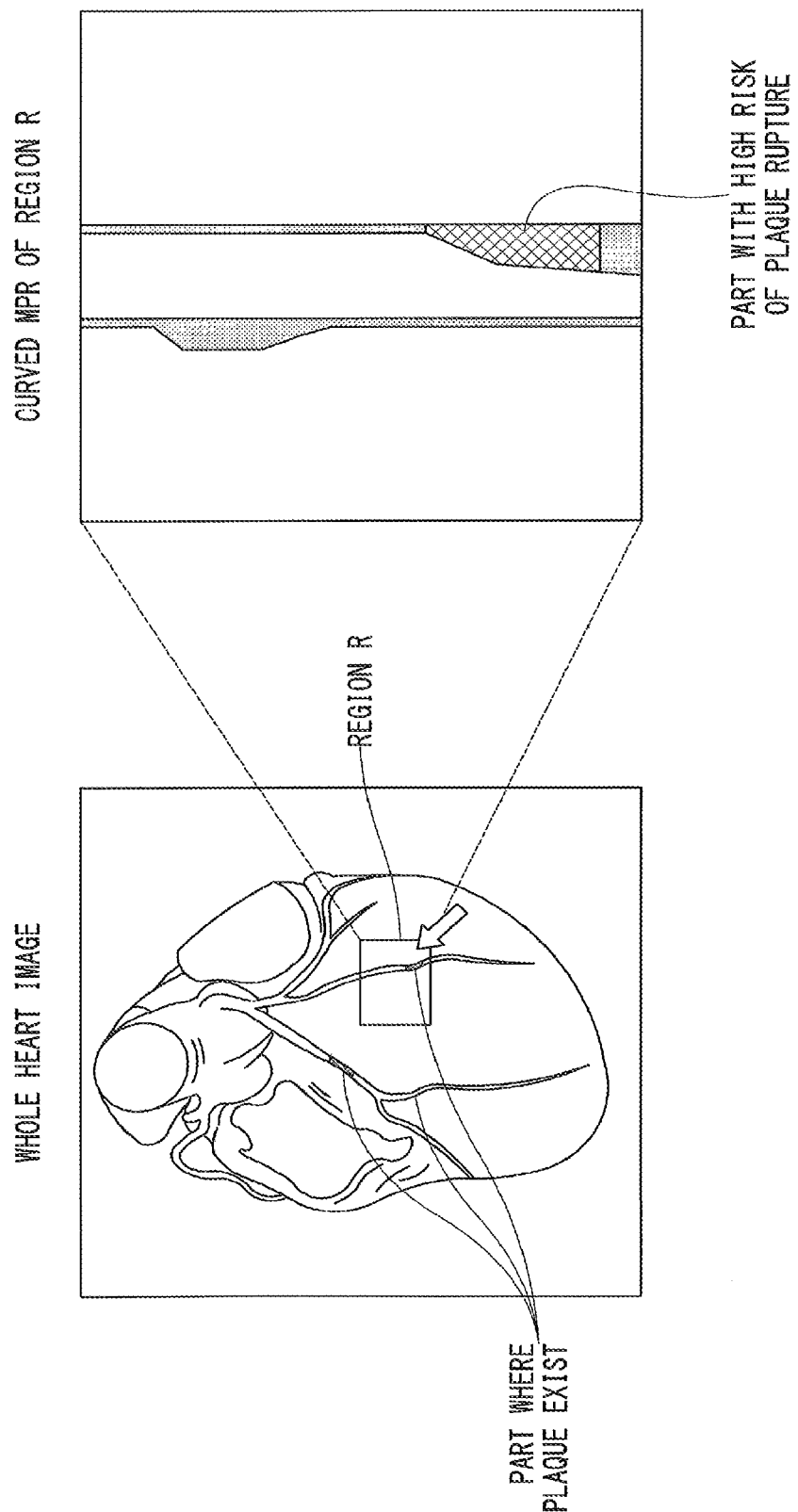
FIG. 12 is a schematic diagram illustrating an image to be displayed according to the image processing device of the third embodiment.

FIG. 12 is a schematic diagram illustrating an image to be displayed according to the image processing device 100 of the third embodiment. FIG. 12 illustrates a case where an analysis result of plaque rupture risk in FIG. 11A and FIG. 11B is superimposed on a whole heart image.

As shown in FIG. 12, an analysis result of plaque rupture risk is indicated by, e.g., colors different from each other and/or a mark to be added on a whole heart image and/or a coronary-artery vessel-wall image of an arbitrary time phase. The left part of FIG. 12 illustrates a case where an existing part of a plaque is displayed in a whole heart image from a bird's eye perspective. The right side of FIG. 12 illustrates a case where the existing part of the plaque of the region R selected in the region R is displayed by curved MPR. In the curved MPR of the region R on the right side of FIG. 12, the part with higher risk of plaque rupture is indicated by a grid-like hatching.

In the whole heart image on the left side of FIG. 12, the part with higher risk of plaque rupture may be indicated by a chromatic color different from colors assigned to normal regions.

Additionally, deformation volume of a plaque between respective time phases may be displayed so that such deformation volume is superimposed on a whole heart image and a coronary-artery vessel-wall image of each time phase. On the basis of deformation volume of a plaque between respective time phases, for instance, which timing in each cardiac beat period deformation volume is maximized can be displayed. Additionally, a user may comprehensively evaluate plaque rupture risk based on such display.

As described above, according to the image processing device 100 of the third embodiment, plaque rupture risk can be analyzed on the basis of deformation volume of a coronary-artery vessel-wall. Thus, a user can observe time-sequential change of a coronary-artery vessel-wall in addition to tissue distribution and a structure of a coronary-artery vessel-wall, and more detailed analysis can be achieved.

Fourth Embodiment

The fourth embodiment relates to a method of performing fluid analysis of calculating FFR (Fractional Flow Reserve) in addition to analysis of plaque rupture risk in the third embodiment. FFR is an index of estimating degree of interruption of bloodstream in downstream of stenosis, which interruption is caused by stenosis in a blood vessel. FFR is calculated by estimating pressure on a blood vessel around stenosis including its upstream and downstream sides.

Figure 13:
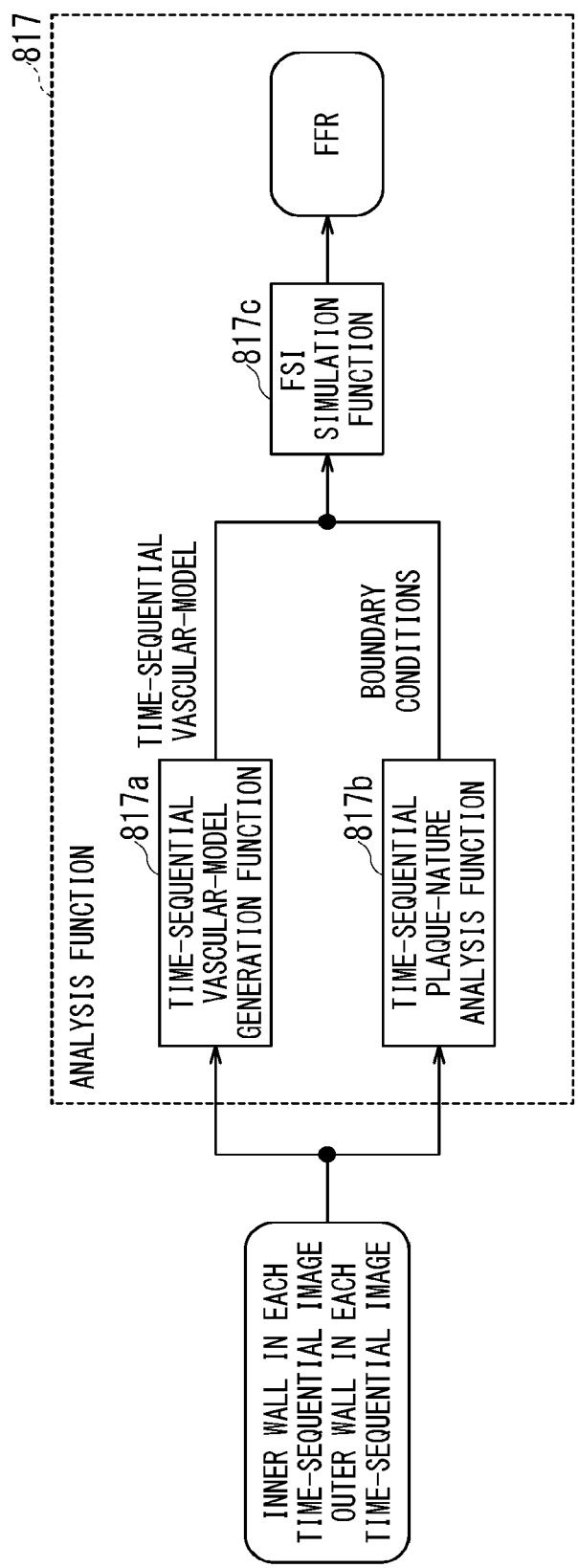
FIG. 13 is a block diagram illustrating fluid analysis according to the image processing device of the fourth embodiment.

FIG. 13 is a block diagram illustrating fluid analysis according to the image processing device 100 of the fourth embodiment. FIG. 13 illustrates the function of the analysis function 817 shown in the block diagram of FIG. 8 in detail.

When time-sequential information on a vascular inner-wall and a vascular outer-wall is inputted to the time-sequential vascular-model generation function 817a of the analysis function 817, the time-sequential vascular-model generation function 817a generates a time-sequential vascular model. A time-sequential vascular model is a series of vessel wall images which are time-sequentially generated and are indicative of temporal change in shape of a vessel wall.

Similarly, time-sequential information on a vascular inner-wall and a vascular outer-wall is inputted to the time-sequential plaque-nature analysis function 817b of the analysis function 817. The time-sequential plaque-nature analysis function 817b is a function of calculating deformation volume of a coronary-artery vessel-wall described in the third embodiment.

When time-sequential information on a vascular inner-wall and a vascular outer-wall is inputted to the time-sequential plaque-nature analysis function 817b, the time-sequential plaque-nature analysis function 817b calculates boundary conditions. The boundary conditions are input values used for of FSI (Fluid Structure Interaction) analysis. The boundary conditions are inflow volume of blood flowing into the blood vessel of analysis target and outflow volume of blood flowing out of the blood vessel of analysis target. The inflow volume of blood flowing into the blood vessel can be easily calculated from blood volume flowing into the target blood vessel. Contrastively, it is difficult to accurately estimate outflow volume flowing out of the target blood vessel, because most blood vessels includes plural branching points. However, the boundary condition on the outflow side is correlated with temporal deformation volume of a vessel wall, and the boundary condition on the outflow side can be accurately calculated on the basis of deformation volume of a vessel wall calculated by the time-sequential plaque-nature analysis function 817b.

Incidentally, FFR is calculated on the basis of a CT image in conventional technology. In X-ray CT imaging, there is a limit in number of images which can be acquired in one cardiac beat period due to restriction in terms of X-ray exposure. Contrastively, MRI has no restriction in terms of X-ray exposure. Thus, in MRI, more images can be acquired for each cardiac beat period and the boundary conditions can be more accurately calculated than CT imaging.

As shown in FIG. 13, the time-sequential vascular model and the boundary conditions calculated in the above-described manner are inputted to an FSI simulation function 817c of the analysis function 817. The FSI simulation function 817c can calculate pressure applied to a vessel wall by bloodstream on the basis of analysis in which cross-interaction between blood fluidity and deformation of the vessel wall is reflected. The analysis function 817 calculates FFR based on the pressure calculated by such FSI simulation.

Additionally, an image indicative of time-sequential analysis result of pressure distribution applied to a vessel wall by bloodstream can be generated on the basis of FSI simulation. For instance, an effect of stent placement in a blood vessel can be visually recognized by an image visualizing pressure distribution in addition to FFR.

As described above, according to the image processing device 100 of the fourth embodiment, FFR can be measured more accurately than conventional technology. Additionally, relationship between blood flow and deformation of a vessel wall can be visually displayed by FSI simulation.

Fifth Embodiment

Although the technology of the present disclosure is applied to the image processing device 100 in the first to fourth embodiments, the technology of the present disclosure is not limited to an image processing device but can be applied to other devices or apparatuses. For instance, extraction of a wall of a tubular structure in the above-described embodiments can be applied to image processing in an MRI apparatus.

Figure 14:
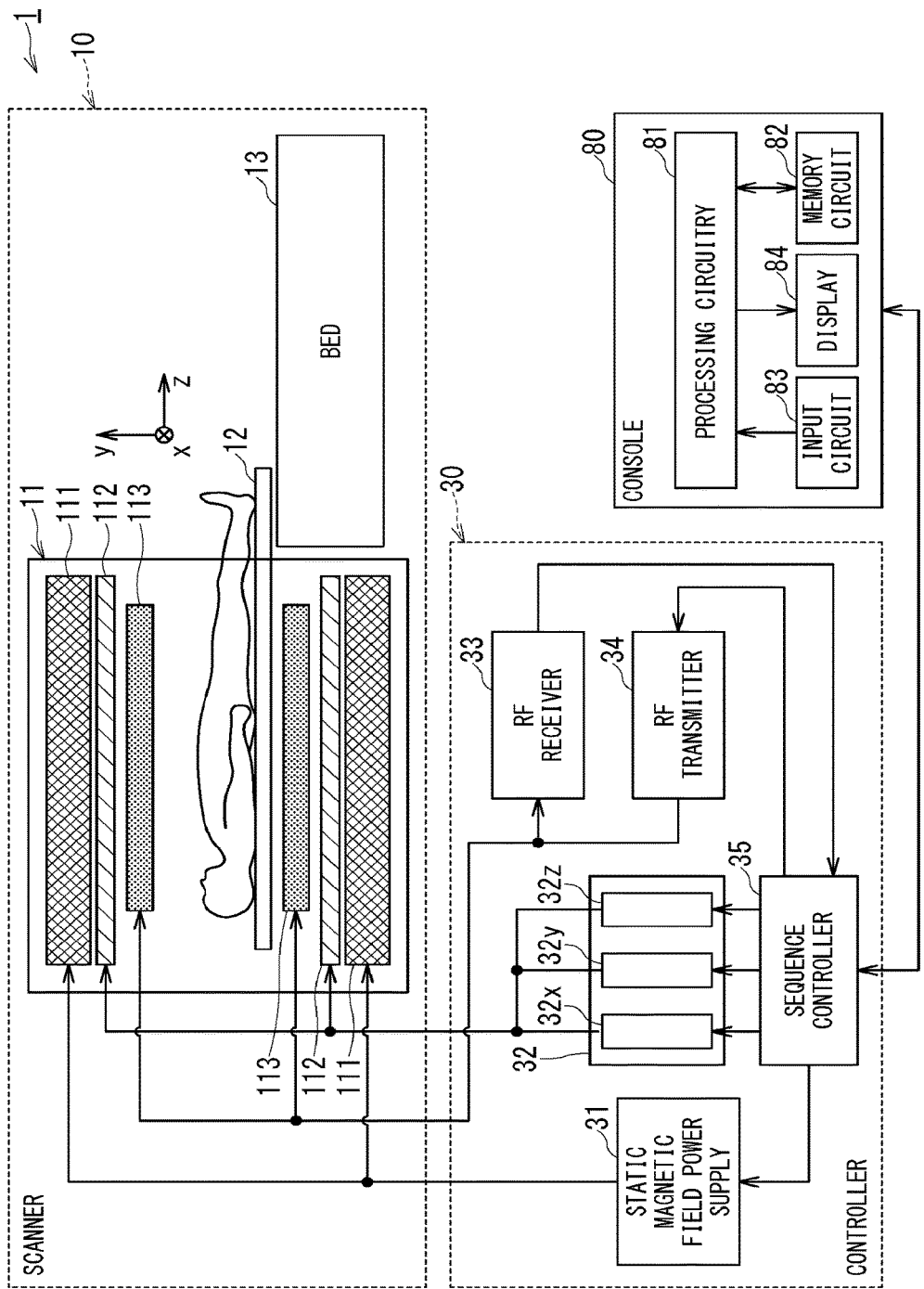
FIG. 14 is a block diagram illustrating overall configuration of the MRI apparatus of the fifth embodiment.

FIG. 14 is a block diagram illustrating overall configuration of the MRI apparatus of the fifth embodiment. The MRI apparatus 1 includes a scanner 10, a controller 30, and a console 80.

The scanner includes a gantry 11 which is substantially in the form of a cylinder.

The gantry 11 includes a static magnetic field magnet 111, a gradient coil 112, an RF (Radio Frequency) coil 113, a table 12, and a bed 13.

Additionally, the controller 30 include a static magnetic field power supply 31, gradient coil power supplies (32$x$ for the X-axis, 32$y$ for the Y-axis, and 32$z$ for the Z-axis), an RF receiver 33, an RF transmitter 34, and a sequence controller 35.

The static magnetic field magnet 111 is substantially in the form of a cylinder. The static magnetic field magnet 111 generates a static magnetic field inside the bore, which is an internal space of the cylindrical structure thereof and functions as an imaging space.

The static magnetic field magnet 111 includes a superconductive coil inside, and this superconductive coil is cooled down to an extremely low temperature by liquid helium. The static magnetic field magnet 111 generates a static magnetic field by supplying the superconductive coil with electric current provided from the static magnetic field power source 31 in an excitation mode. Afterward, when the static magnetic field magnet 111 shifts to a permanent current mode, the static magnetic field power source 31 is separated. Once it enters the permanent current mode, the static magnetic field magnet 111 continues to generate a strong static magnetic field for a long time, e.g., over one year. Incidentally, the static magnetic field magnet 111 may be configured as a permanent magnet.

The gradient coil 112 is also substantially in the form of a cylinder and is fixed to the inside of the static magnetic field magnet 111. This gradient coil 112 applies gradient magnetic fields to the imaging space in the respective directions of the X-axis, the Y-axis, and the Z-axis of the apparatus coordinate system, by using the electric currents supplied from the gradient coil power supplies 32$x$, 32$y$, and 32$z$.

The RF coil 113 is also called a whole body coil, and is fixed to the inside of the gradient coil 112. The RF coil 113 applies RF pulses transmitted from the RF transmitter 34 to an object, and receives MR (Magnetic Resonance) signals emitted from the object due to excitation of hydrogen atoms.

The bed 13 can move the table 12 in the upward and downward directions along the vertical direction (i.e., the Y-axis direction in the apparatus coordinate system), and moves the object loaded on the table 12 to a predetermined height before imaging. Afterward, at the time of imaging, the bed 13 moves the table 12 in the horizontal direction, i.e., in the axis direction of the cylindrical structure of the gantry 11 so as to move the object inside the bore. Here, the vertical direction is the Y-axis direction in the apparatus coordinate system, and the horizontal direction is the Z-axis direction in the apparatus coordinate system.

The RF transmitter 34 transmits RF pulses to the RF coil 113 based on a command from the sequence controller 35. The RF receiver 33 receives MR signals received by the RF coil 113, and transmits raw data obtained by digitizing the received MR signals to the sequence controller 35.

The sequence controller 35 performs a scan of an object under the control of the console 80, by driving each of the gradient coil power supplies (32$x$, 32$y$, and 32$z$), the RF transmitter 34, and the RF receiver 33 so as to acquire raw data. When the sequence controller 35 receives the raw data from the RF receiver 33 by performing the scan, the sequence controller 35 transmits the raw data to the console 80.

Here, the console 80 which controls the entirety of the MRI apparatus 1 is configured on the basis of a computer, and can intercommunicate with an external device via an network such as a LAN. The console 80 includes, e.g., processing circuitry 81, a memory circuit 82, an input circuit 83, and a display 84 as hardware components. The processing circuitry 81 is interconnected with respective hardware components constituting the console 80 via a bus as a transmission path of common signals. Incidentally, the console 80 is equipped with a memory-medium drive in some case.

The console 80 shown in FIG. 14 performs various types of image reconstruction processing and display control, and has functions equivalent to the above-described image processing device 100. Thus, the console 80 of the MRI apparatus 1 can execute the same operations as the operations of the image processing device 100 described with reference to FIG. 1 to FIG. 13.

Although a description has been given of a case where a wall of a coronary artery as a tubular structure is extracted in the above-described embodiments, embodiments of the present disclosure are not limited to such a case. The technology of extracting a wall of a tubular structure can be applied to another tissue having a tubular structure such as a carotid artery and a lymph vessel.

According to the image processing device or the MRI apparatus in at least one of the above-described embodiments, a wall of a tubular structure can be precisely identified.

Incidentally, the memory circuit 82 is an aspect of the memory circuitry recited in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:
1. An image processing device, comprising:
 processing circuitry configured to acquire a fat image obtained using a water/fat separation method of magnetic resonance imaging,
extract an outer wall image of a tubular structure out of the fat image, and
generate a tubular-structure wall image in which a wall of the tubular structure is distinguished, based on the extracted outer wall image.

2. The image processing device according to claim 1, wherein the processing circuitry is further configured to
acquire a water image obtained using the water/fat separation method of magnetic resonance imaging,
extract an inner wall image of the tubular structure out of the water image, and
generate the tubular-structure wall image based on the extracted outer wall and the extracted inner wall.

3. The image processing device according to claim 2, wherein the processing circuitry is further configured to generate an image in which the tubular-structure wall image and a three-dimensional image depicting an entirety of a heart are associated with each other.

4. The image processing device according to claim 2, wherein the processing circuitry is further configured to
analyze tissue characterization of the wall of the tubular structure, and
generate an image in which an analysis result of the tissue characterization is superimposed on the wall of the tubular structure.

5. The image processing device according to claim 4, wherein the processing circuitry is further configured to
extract the inner wall image out of each of plural water images of respective time phases,
extract the outer wall image out of each of plural fat images of the respective time phases, and
generate tubular-structure wall images of the respective time phases, in each of which the inner wall image and the outer wall image are distinguished.

6. The image processing device according to claim 4, wherein the processing circuitry is further configured to
determine a type of tissue characterization for each of plural regions of the tubular structure as one of normal, fibrosis, fat accumulation, and calcification, by analyzing the tissue characterization of the tubular structure, and
generate an image in which plural colors different from each other are assigned to the plural regions of the tubular structure, according to the type of tissue characterization for each of plural regions.

7. The image processing device according to claim 6, wherein the processing circuitry is further configured to
extract the inner wall image out of each of plural water images of respective time phases,
extract the outer wall image out of each of plural fat images of the respective time phases, and
generate tubular-structure wall images of the respective time phases, in each of which the inner wall image and the outer wall image are distinguished.

8. The image processing device according to claim 7, wherein the processing circuitry is further configured to
analyze a plaque rupture risk for a plaque existing in tubular-structure wall images of plural time phases, based on tissue characterization of the wall of the tubular structure and a deformation volume of the plaque between the plural time phases, and
generate an image in which information on an analysis result of the plaque rupture risk is included.

9. The image processing device according to claim 7, wherein the processing circuitry is further configured to
perform fluid structure interaction analysis by using a deformation volume between the tubular-structure wall images of the respective time phases and tissue characterization of the wall of the tubular structure, and
generate an image in which information on an analysis result of the fluid structure interaction analysis is included.

10. The image processing device according to claim 2, wherein the processing circuitry is further configured to
calculate FFR (Fractional Flow Reserve) by using a deformation volume between tubular-structure wall images of plural time phases and tissue characterization of the wall of the tubular structure, and
generate an image in which information on the calculated FFR is included.

11. The image processing device according to claim 2, wherein the processing circuitry is further configured to
analyze a plaque rupture risk for a plaque existing in tubular-structure wall images of plural time phases, based on tissue characterization of the wall of the tubular structure and a deformation volume of the plaque between the plural time phases, and
generate an image in which information on an analysis result of the plaque rupture risk is included.

12. The image processing device according to claim 2, wherein the processing circuitry is further configured to
perform fluid structure interaction analysis by using a deformation volume between tubular-structure wall images of plural time phases and tissue characterization of the wall of the tubular structure, and
generate an image in which information on an analysis result of the fluid structure interaction analysis is included.

13. The image processing device according to claim 2, wherein the processing circuitry is further configured to generate the tubular-structure wall image based on the outer wall image and the inner wall image, which is extracted by a method other than the water/fat separation method of magnetic resonance imaging.

14. The image processing device according to claim 2, further comprising a display configured to display the tubular-structure wall image.

15. An MRI apparatus, comprising:
an RF coil configured to receive magnetic resonance signals under a water/fat separation method; and
processing circuitry configured to
reconstruct a water image and a fat image from the magnetic resonance signals under the water/fat separation method,
acquire a fat image obtained using the water/fat separation method of magnetic resonance imaging,
extract an inner wall image of a tubular structure out of the water image,
extract an outer wall image of the tubular structure out of the fat image, and
generate a tubular-structure wall image in which the tubular structure is distinguished, based on the extracted inner wall image and the extracted outer wall image.

16. The image processing device according to claim 1, wherein the tubular structure is a vessel.

* * * * *